United States Patent
Yamamoto

[11] Patent Number: 6,063,024
[45] Date of Patent: May 16, 2000

[54] OBSERVATION APPARATUS

[75] Inventor: Masao Yamamoto, Tama, Japan

[73] Assignee: Scalar Corp., Tokyo, Japan

[21] Appl. No.: 08/738,409

[22] Filed: Oct. 25, 1996

Related U.S. Application Data

[62] Division of application No. 08/485,072, Jun. 7, 1995, abandoned, which is a continuation of application No. 08/102,455, Aug. 5, 1993, abandoned.

[30] Foreign Application Priority Data

| Nov. 19, 1992 | [JP] | Japan | 4-332235 |
| Feb. 23, 1993 | [JP] | Japan | 5-056380 |

[51] Int. Cl.⁷ ................................................ A61B 1/07
[52] U.S. Cl. ................... 600/160; 600/178; 600/182
[58] Field of Search ............................... 600/130, 160, 600/178, 181, 182

[56] References Cited

U.S. PATENT DOCUMENTS

| 2,633,122 | 3/1953 | Vannas | 128/6 |
| 3,753,607 | 8/1973 | Kitano et al. | 385/129 X |
| 3,801,181 | 4/1974 | Kitano et al. | 385/124 |
| 4,711,999 | 12/1987 | Shishido et al. | 128/6 X |
| 4,736,733 | 4/1988 | Adair | 128/6 |
| 4,755,029 | 7/1988 | Okabe | 385/124 X |
| 4,782,819 | 11/1988 | Adair | 600/136 X |
| 4,862,873 | 9/1989 | Yajima et al. | 128/6 |
| 4,905,082 | 2/1990 | Nishigaki et al. | 128/6 X |
| 4,924,854 | 5/1990 | Pritchard | 128/6 |

FOREIGN PATENT DOCUMENTS

| 1254289 | 11/1967 | Germany | 128/6 |
| 2950520 | 6/1980 | Germany | 600/182 |
| 0188513 | 8/1986 | Japan | 128/6 |
| 401207712 | 8/1989 | Japan | 600/181 |
| 0702698 | 1/1954 | United Kingdom | 128/6 |

*Primary Examiner*—John Mulcahy
*Attorney, Agent, or Firm*—Jordan and Hamburg LLP

[57] ABSTRACT

An observation apparatus comprises an illuminating system for illuminating a material-to-be-observed, an elongated image transmitting member for fetching an image of the material-to-be-observed, and an image pickup device for picking up the image of the material-to-be-observed, which has been transmitted by the image transmitting member. The illuminating system is constituted such that illumination light having entered from an output end face of the image transmitting member into the image transmitting member may be irradiated to the material-to-be-observed through propagation inside of the image transmitting member. The slender portion containing the image transmitting member can thereby be made very thin and constituted as a cheap releasable unit, and a site to be observed can be illuminated accurately and efficiently.

4 Claims, 12 Drawing Sheets

OBSERVATION APPARATUS

This application is a division of application Ser. No. 08/485,072, now abandoned, filed Jun. 7, 1995, which is a continuation of application Ser. No. 08/102,455 filed Aug. 5, 1993, now abandoned.

BACKGROUND OF THE INVENTION

This invention relates to an observation apparatus, such as an endoscope for medical purposes or an apparatus used to view internal configurations of various structures and equipment.

Observation apparatuses, such as endoscopes for medical purposes, or bore scopes and image scopes used to view internal configurations of various structures and equipment, are provided with slender portions containing elongated image transmitting member, such distributed index types of image transmitting members or image transmitting members having image fiber or relay lens structures have been used. The slender portion is inserted into a body or a piece of equipment, and the internal configuration of the body or the equipment is thus observed. Therefore, for improved performance of the observation apparatuses, the slender portions should be as thin as possible.

In general, the observation apparatuses are provided with a self-illuminating system having optical fiber bundles, which extend along the slender portions, and which system serves as light guides. The quality of the illuminating system largely affects the performance of the observation apparatuses. Specifically, it is required that a site to be observed can be illuminated accurately and efficiently. Therefore, a high accuracy is required during the processing of illuminating ends of light guides and, as result, the processing cost will inevitably be increased.

Also, in the cases of medical endoscopes, or the like, for the prevention of infection, it is preable that the portions which are expected to come into contact with human body tissues or body fluids, i.e. the slender portions, be constituted as units capable of being released and which are disposable. However, in conventional endoscopes, or the like, the light guides of the self-illuminating systems are mechanically integral with the slender portions, and therefore it is difficult for the slender portions to be constructed as releasable units. Also, even if the slender portions were constructed as releasable units, the increased cost of the slender portions would prohibit use as disposable units.

SUMMARY OF THE INVENTION

The primary object of the present invention is to provide a observation apparatus having a slender portion containing an elongated image transmitting member, and wherein the slender portion is made as thin as possible, a site to be observed is illuminated accurately and efficiently, and the slender portion is capable of easily constituted as a releasable unit.

Another object of the present invention is to provide an observation apparatus having a slender portion containing an elongated image transmitting member, wherein the cost of the slender portion constituted as a releasable unit is kept low, and the releasable unit can thereby be an disposable.

The present invention provides a first observation apparatus comprising an illuminating system for illuminating a material-to-be-observed, an elongated image transmitting member for fetching an image of the material-to-be-observed, and an image pickup device for picking up the image of the material-to-be-observed, which has been transmitted by the image transmitting member. The illuminating system is constituted such that illumination light having entered from an output end face of the image transmitting member into the image transmitting member may be irradiated to the material-to-be-observed through propagation inside of the image transmitting member.

The present invention also provides a second observation apparatus comprising an illuminating system for illuminating a material-to-be-observed, an elongated image transmitting member for fetching an image of the material-to-be-observed, and an image pickup device for picking up the image of the material-to-be-observed, which has been transmitted by the image transmitting member. The illuminating system is constituted such that a translucent mirror is located between an output end face of the image transmitting member and the image pickup device, such that illumination light having been reflected by the translucent mirror may be caused to impinge upon the output end face of the image transmitting member, and such that the illumination light having entered into the image transmitting member may be irradiated to the material-to-be-observed through propagation inside of the image transmitting member.

The present invention further provides a third observation apparatus comprising an illuminating system for illuminating a material-to-be-observed, an elongated image transmitting member for fetching an image of the material-to-be-observed, and an image pickup device for picking up the image of the material-to-be-observed, which has been transmitted by the image transmitting member. Output end faces of a plurality of optical fibers for guiding illumination light from a light source are located annularly along a peripheral edge region of an output end face of the image transmitting member. The illumination light, which has been radiated out of the output end face of each of the optical fibers located annularly, is caused to impinge upon the peripheral edge region of the output end face of the image transmitting member. The illumination light having entered into the image transmitting member is irradiated to the material-to-be-observed through propagation inside of the image transmitting member.

The present invention still further provides a fourth observation apparatus comprising an elongated image transmitting member for fetching an image of a material-to-be-observed, and an illuminating system for illuminating the material-to-be-observed, the illuminating system being constituted such that illumination light given by a light source system may be condensed and caused to enter from an output end face of the image transmitting member into the image transmitting member, and such that the illumination light having entered into the image transmitting member may be irradiated to the material-to-be-observed through propagation inside of the image transmitting member. The light source system is constituted of a light source and a plurality of optical fibers for guiding the illumination light from the light source, the plurality of the optical fibers are grouped into unit bundles, each of which is composed of an appropriate number of the optical fibers, leading ends of the unit bundles being located annularly, condensing lenses are located at positions such that they may correspond to the annular location of the unit bundles, and the illumination light coming from the optical fibers is condensed by the annularly located condensing lenses to a peripheral edge region of the output end face of the image transmitting member such that the condensed spots of the illumination light may annularly impinge upon the peripheral edge region of the output end face of the image transmitting member.

The present invention also provides a fifth observation apparatus comprising an elongated image transmitting member for fetching an image of a material-to-be-observe(l, and an illuminating system for illuminating the material-to-be-observed, the illuminating system being constituted such that illumination light given by a light source system may be condensed and caused to enter from an output end face of the image transmitting member into the image transmitting member, and such that the illumination light having entered into the image transmitting member may be irradiated to the material-to-be-observed through propagation inside of the image transmitting member. A distributed index type of light transmitting member is employed in the light source system, the light transmitting member comprising an elongated small-diameter portion, a large-diameter portion, which is integrally combined with an end of the small-diameter portion, and a continuous diameter change portion, which is located between the small-diameter portion and the large-diameter portion, and the diameter of which changes continuously, the state of distribution of refractive index in the continuous diameter change portion changing continuously in accordance with the continuous change in the diameter, and the illumination light, which has been entered from an end face of the large-diameter portion into the light transmitting member and which has then been radiated out of an end face of the small-diameter portion, is caused to impinge upon the output end face of the image transmitting member.

The present invention further provides a sixth observation apparatus comprising an elongated image transmitting member for fetching an image of a material-to-be-observed, and an illuminating system for illuminating the material-to-be-observed, the illuminating system being constituted such that illumination light given by a light source system may be condensed and caused to enter from an output end face of the image transmitting member into the image transmitting member, and such that the illumination light having entered into the image transmitting member may be irradiated to the material-to-be-observed through propagation inside of the image transmitting member. A cylindrical transparent member is employed in the light source system, the cylindrical transparent member having a predetermined wall thickness and comprising one end side having a large diameter and the other end side having a small diameter, the diameter of the cylindrical transparent member changing continuously from the large-diameter side to the small-diameter side, and the illumination light, which has been entered from an end face on the large-diameter side of the cylindrical transparent member into the cylindrical transparent member and which has then been radiated out of an end face on the small-diameter side of the cylindrical transparent member, is caused to impinge upon a peripheral edge region of the output end face of the image transmitting member.

With the first to sixth observation apparatuses in accordance with the present invention, the image transmitting member, which acts as an image transmitting path, also serves as the propagation path for the illumination light. The illumination light, which has entered from the output end face of the image transmitting member into the image transmitting member, is propagated in the direction reverse to the direction along which image light travels. The illumination light is then radiated out of an input end face of the image transmitting member and illuminates the material-to-be-observed. As a result, the image fetching range and the illumination range coincides with each other, and the site from which an image is to be obtained, can be illuminated accurately and efficiently. Also, a light guide need not be located along a slender portion as with the conventional technique. Therefore, the slender portion can be made thinner than in the conventional observation apparatus. Additionally, with the observation apparatuses in accordance with the present invention, the major element of the slender portion is composed of only the image transmitting member. Therefore, the slender portion can be easily constituted as a releasable unit, and the cost can be kept low. Further, even if the leading end of she image transmitting member or the leading end of an optical element, which is located at the leading end of the image transmitting member, is brought into direct contact with the surface of the material-to-be-observed, sufficiently effective illumination can be given to the material-to-be-observed. Therefore, the material-to-be-observed can be observed while the leading end of the image transmitting member is in contact with the material-to-be-observed. Such contact observation operation is particularly important when surfaces of internal organs, and the like are to be observed. For example, by removing mucus from the surface of an internal organ, an image representing the surface of the internal organ can be obtained more accurately.

in cases where the optical fibers and the condensing lenses are combined with each other, illumination light having a high intensity can be fed into the image transmitting member such that interference adversely affecting the image transmission is prevented. Specifically, the illumination light coming from the optical fiber is condensed by the annularly located condensing lenses to the peripheral edge region of the output end face of the image transmitting member such that the condensed spots of the illumination light may annularly impinge upon the peripheral edge region of the output end face of the image transmitting member. In this manner, the peripheral edge region of the image transmitting member is utilized efficiently. Therefore, illumination light having a high intensity can be fed into the image transmitting member without adversely affecting the image light, which is radiated out of the output end face of the image transmitting member.

In cases where the light transmitting member, having the continuous diameter change portion is utilized, illumination light having a very high intensity can be fed into the image transmitting member using a simple structure. Also, in the observation apparatus described above, no interference occurs in the image transmitting system. Specifically, this light transmitting member has the self-condensing function by virtue of the continuous diameter change portion, and the illumination light having entered from the large-diameter portion is radiated as strong condensed light out of the small-diameter portion. Therefore, the illumination light having a high intensity can be fed into the image transmitting member. Also, in cases where the small-diameter portion is very thin having a diameter not larger than 1 mm, even if the small-diameter portion overlaps upon the output end face of the image transmitting member, adverse effects of such location of the small-diameter portion on the image light, which is radiated out of the output end face of the image transmitting member, can be ignored. Therefore, the simplest structure can be employed wherein the end face of the small-diameter portion is located in a position facing the center region of the output end face of the image transmitting member, and wherein the illumination light is thereby irradiated into the image transmitting member.

In cases where the cylindrical transparent member is utilized, a simpler structure can be employed in order to cause the illumination light, which has been guided from the light source through the optical fibers, to impinge upon the output end face of the image transmitting member. In addition illumination light having a higher intensity can be obtained. Specifically, in cases where the leading ends of the optical fibers are accurately trued up and located facing the output end face of the image transmitting member having a small diameter, high levels of processing techniques are required. However, in cases where the cylindrical transparent member is utilized, the leading ends of the optical fibers may be trued up so as to match the large-diameter side of the cylindrical transparent member, and therefore the processing can be markedly simplified. Also, the illumination light, which has entered from the wide area on the large-diameter side into the cylindrical transparent member, is condensed in accordance with the continuous diameter change from the large-diameter side to the small-diameter side, and is radiated out of the small-diameter side having a narrow area. Accordingly, illumination light having a higher intensity can be obtained than when the leading ends of the optical fibers are located so as to stand directly facing the output end face of the image transmitting member.

In the aforesaid observation apparatuses in accordance with the present invention, a distributed index type of image transmitting member should preferably be employed as the elongated image transmitting member. Besides the distributed index type of image transmitting member, the image fiber type of image transmitting member, the relay type of image transmitting member, or the like, may be employed.

These and other objects, features and advantages of the invention will become more apparent upon a reading of the following detailed specification and drawings.

DESCRIPTION OF THE PREFERRED EMBODIMENTS

Figure 3:
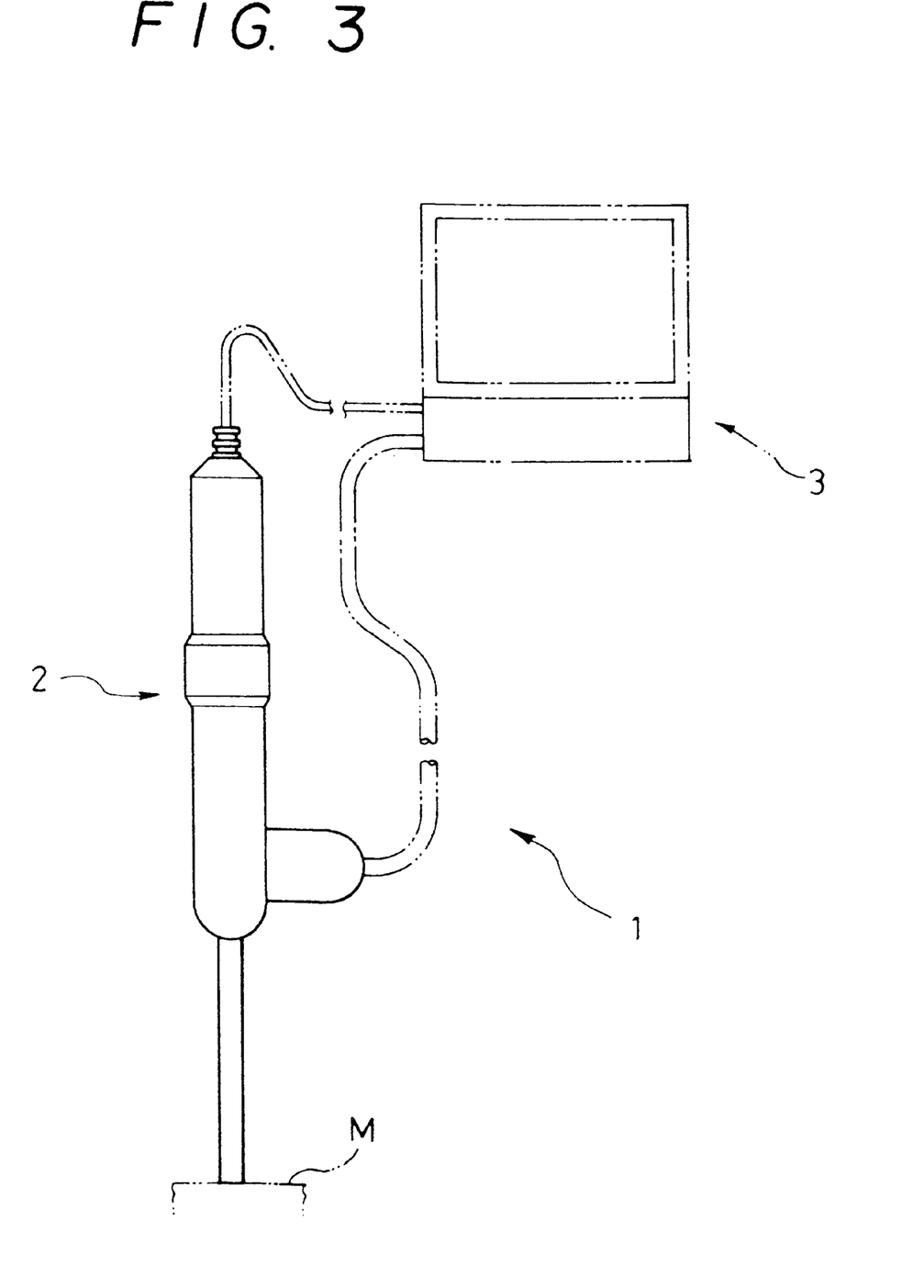
FIG. 3 is a side view showing the first embodiment of the observation apparatus in accordance with the present invention.

The present invention will hereinbelow be described in further detail with reference to the accompanying drawings.
First Embodiment:

In the first embodiment of the observation apparatus in accordance with the present invention, as illustrated in FIG. 3, an observation apparatus 1 comprises an objective section 2, and an observation apparatus body 3, which contains a display for reproducing a visible image from an image fetched by the objective section 2.

Figure 1:
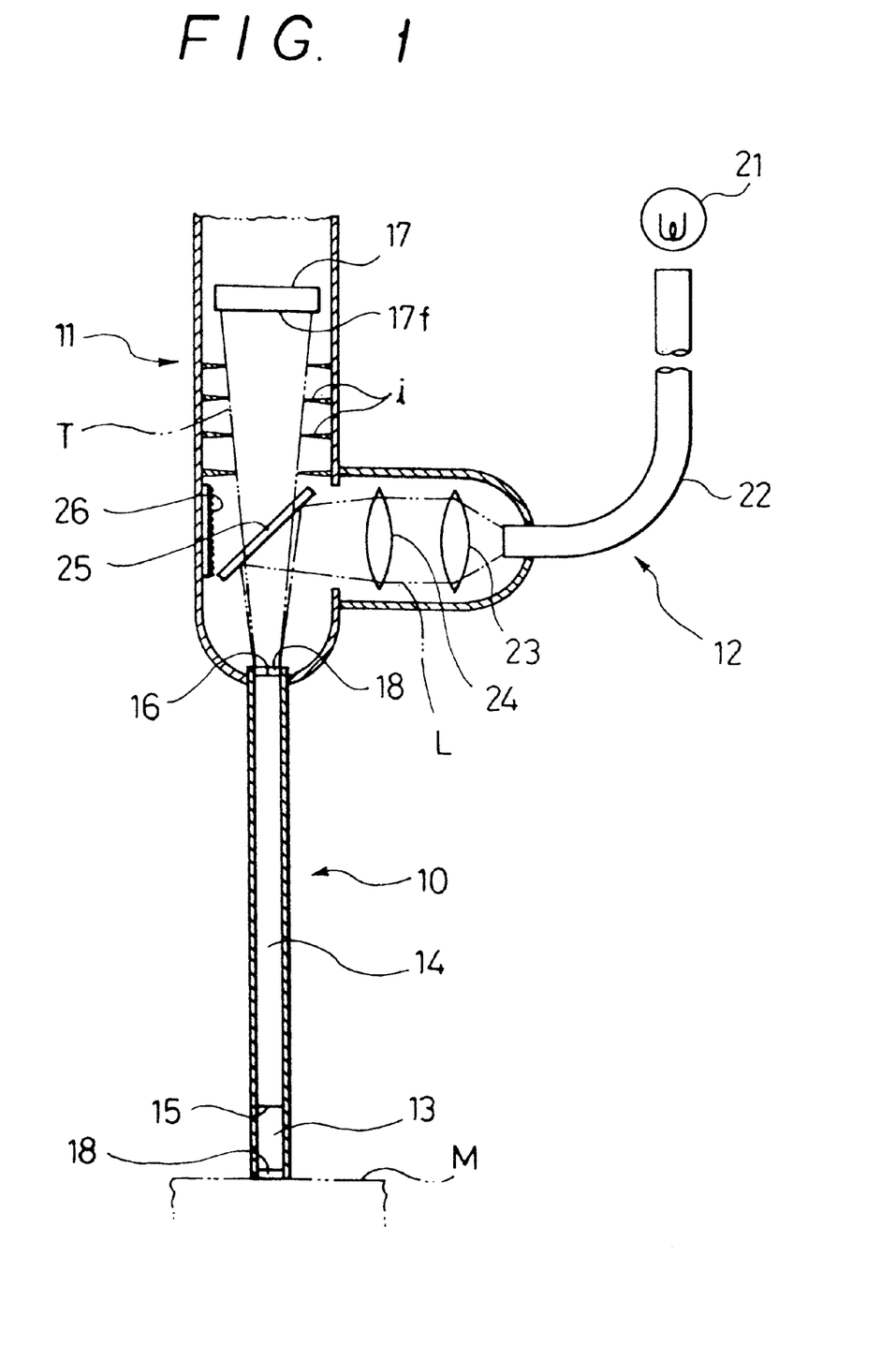
FIG. 1 is a sectional view showing the major part of a first embodiment of the observation apparatus in accordance with the present invention.

As illustrated in FIG. 1, the objective section 2 is provided with an image transmitting system 10 for fetching the image of a material-to-be-observed M1, an image pickup system 11 for picking up the image obtained by the image transmitting system 10, and an illuminating system 12 for feeding illumination light.

The image transmitting system 10 is provided with an elongated image transmitting member 14, and an objective lens 13 connected to a leading end of the image transmitting member 14. Cover glass plates 18, 18 are respectively located at the leading end of the objective lens 13 and the tail end of the image transmitting member 14.

Figure 2:
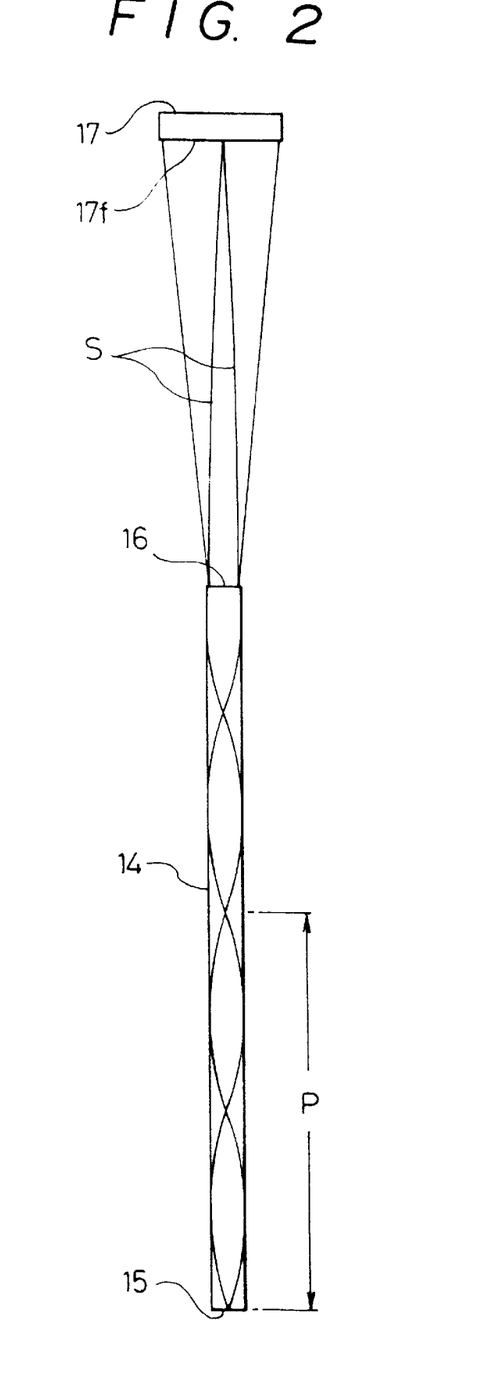
FIG. 2 is a side view showing how light is transmitted through a image transmitting member.

In the preferred embodiment, the image transmitting member 14 is a distributed index type of image transmitting member, in which the refractive index is distributed in a parabolic pattern from the center axis towards the outer circumference, and which has a cylindrical rod-like shape. As illustrated in FIG. 2, light is propagated along a sinusoidal optical path corresponding to the state of distribution of the refractive index, and an image is directly transmitted from an input end face 15 towards an output end face 16.

The image transmitting member 14 has a length having the relationship with respect to a pitch length P of the period of the meandering of the optical path, which relationship is expressed as $(n+X) \times P$ (mm), wherein $n=0, 1, 2, 3, \ldots$, and X is approximately 0.8. As a result, as illustrated in FIG. 2, the image of the material-to-be-observed M, which image has been formed on the input end face 15 by the objective lens 13 shown in FIG. 1, can be formed at a position outward from the output end face 16, i.e. at the position at which the tangential lines S, S with respect to the optical path curves intersect with each other. Therefore, when a light receiving face 17f of a solid-state image pickup device 17 is located facing the position of image formation, the image of the material-to-be-observed M can be formed directly on the light receiving face 17f.

The direct image formation on the light receiving face 17f of the solid-state image pickup device 17 by the image formation outside of the output end face has the advantages described below over the image formation on the output end face, which image formation is carried out in the conventional distributed index type of image transmitting member. Specifically, in the cases of the image formation on the output end face, the image having been formed on the output end face is again formed via an eyepiece, and therefore the problems of chromatic aberration of the eyepiece occur. In the cases of the image formation outside of the output end face, such problems can be eliminated. Also, because no eyepiece is required, the structure can be simplified. Further, where the image is formed outside of the output end face, an image having good quality can be obtained reliably without being adversely affected by the accuracy with which the output end face is polished, or dust sticking to the output end face.

The image pickup system 11 contains the image pickup means (in this embodiment, a CCD) 17, and a means (not shown) for controlling the CCD 17. A plurality of flare stops i, i, . . . are annularly projected into the optical path, which extend from the image transmitting member 14, such that a minimum necessary optical path T may be formed.

The illuminating system 12 is composed of an optical fiber bundle 22, which guides the illumination light from a light source lamp 21 located in the observation apparatus body 3, intermediate lenses 23 and 24, and a translucent mirror 25. The illumination light L coming from the intermediate lens 24 impinges upon the translucent mirror 25 from a direction, which perpendicularly intersects with the optical path T extending from the output end face 16 of the image transmitting member 14 to the CCD 17. The direction of travel of an approximately one-half portion of the illumination light L is changed 90° by the translucent mirror 25, and this portion of the illumination light L impinges upon the output end face 16 of the image transmitting member 14.

A light absorbing screen 26 is located at the back of the translucent mirror 25 in order to absorb the illumination light which has passed through the translucent mirror 25, to prevent the illumination light from adversely affecting the CCD 17. The term "translucent mirror" as used herein refers to a mirror which reflect a portion of light impinging thereupon and transmits the remainder of light.

Figure 4:
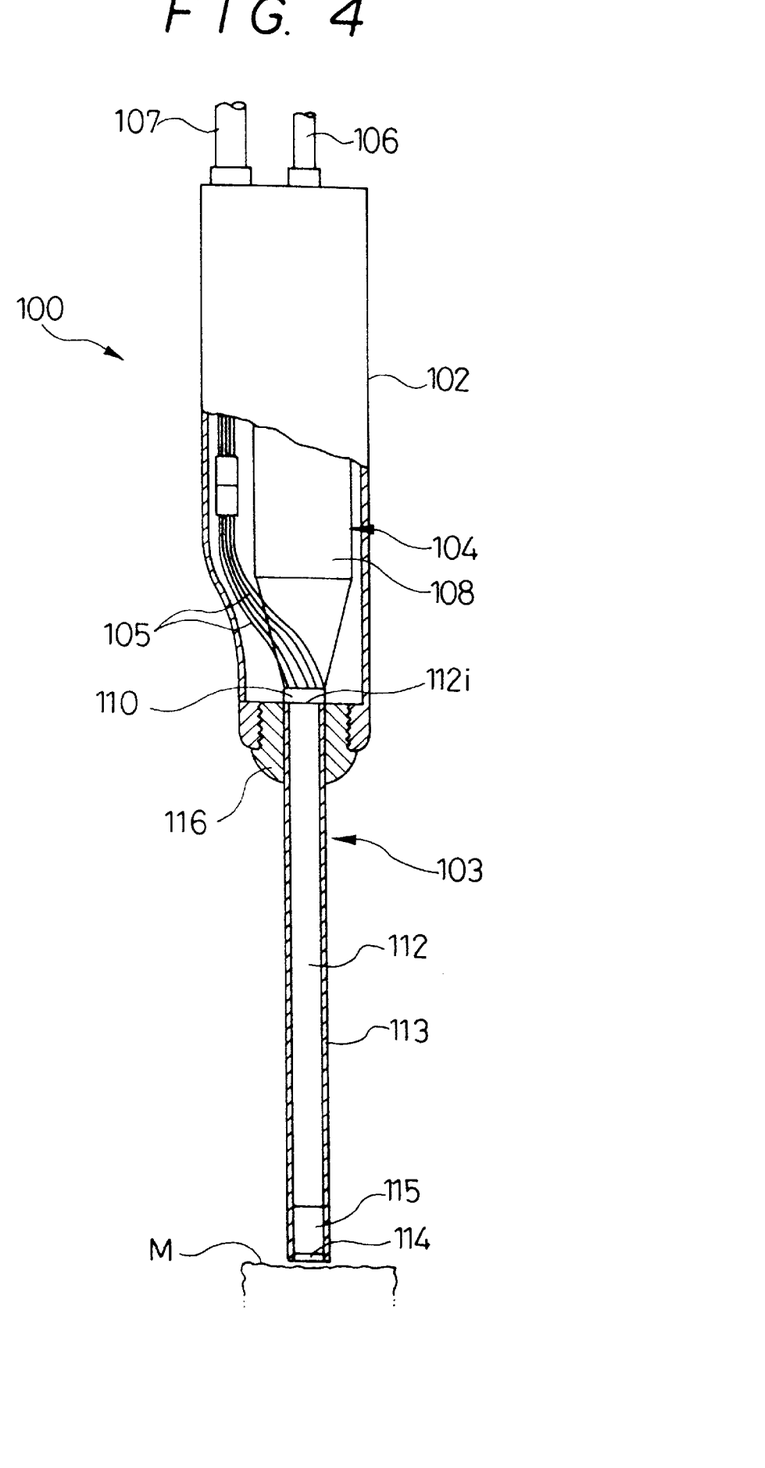
FIG. 4 is a partially sectional side view showing an image pickup section in a second embodiment of the observation apparatus in accordance with the present invention.

Second Embodiment:

In the second embodiment of the observation apparatus in accordance with the present invention, as illustrated in FIG. 4, an image pickup section 100 comprises a main body 102 and an image transmitting member unit 103. The image of the material-to-be-observed M, which has been picked up by the image pickup section 100, is reproduced into a visible image by a observation apparatus body (not shown), which corresponds to the observation apparatus body 3 employed in the first embodiment as shown in FIG. 3.

The main body 102 has a cylindrical shape and incorporates an image pickup unit 104 therein. A plurality of optical fibers 105, 105, . . . constituting a light source system extend inside of the main body 102. Also, a signal cable 106, which is connected to the image pickup unit 104, and a light source cable 107, which is composed of a bundle of the optical fibers 105, 105, . . . , extend from the main body 102 to the exterior.

Figure 5:
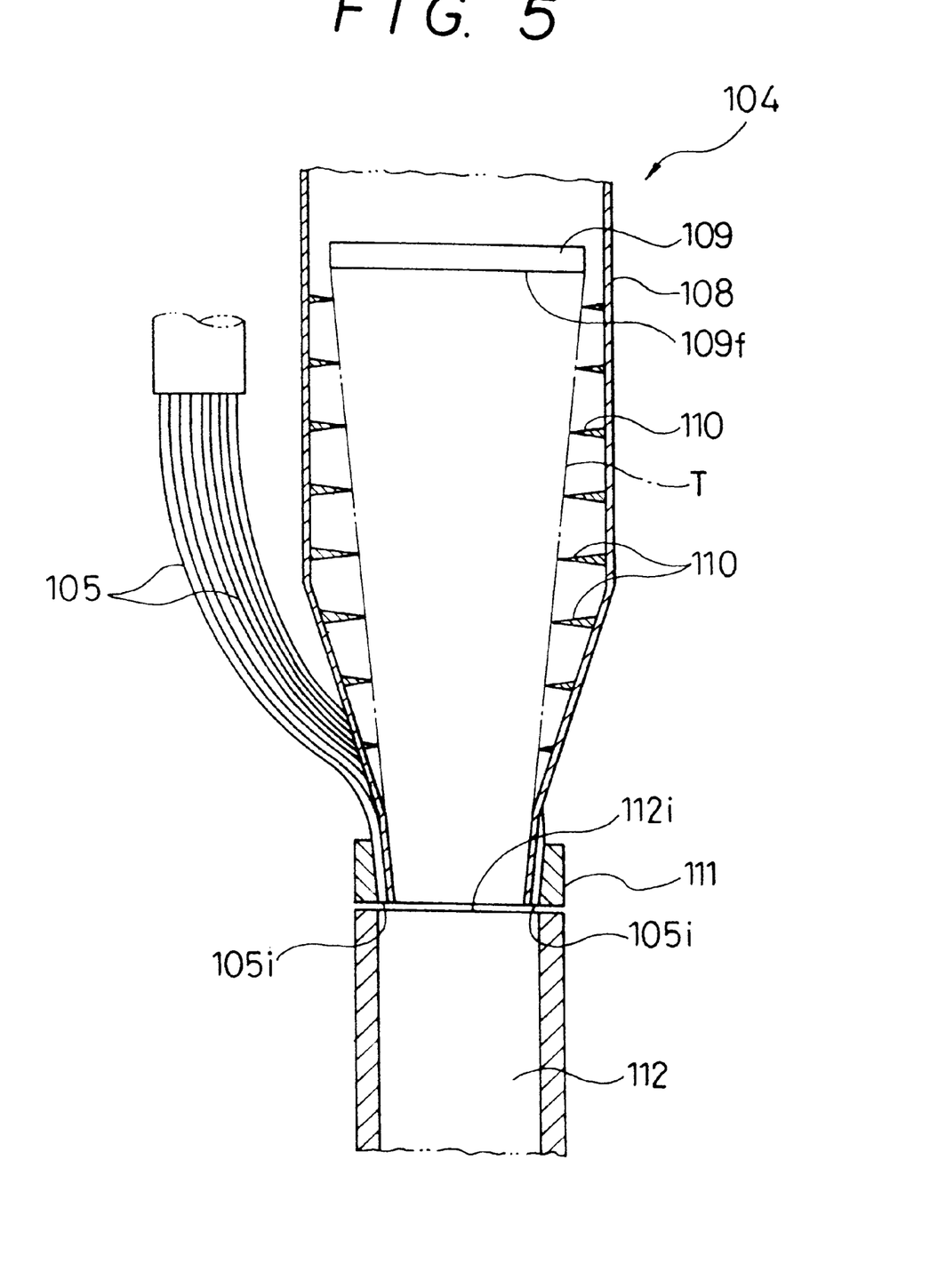
FIG. 5 is an enlarged sectional view showing part of the image pickup section shown in FIG. 4.

As illustrated in detail in FIG. 5, the image pickup unit 104 comprises a light shielding cylinder 108, having a conically narrowed leading end portion. A solid-state image pickup device 109 of a camera unit, flare stops 110, 110, . . . for giving minimum necessary image optical path T to a light receiving face 109f of the solid-state image pickup device 109, and the like, are located within the light shielding cylinder 108.

Figure 6:
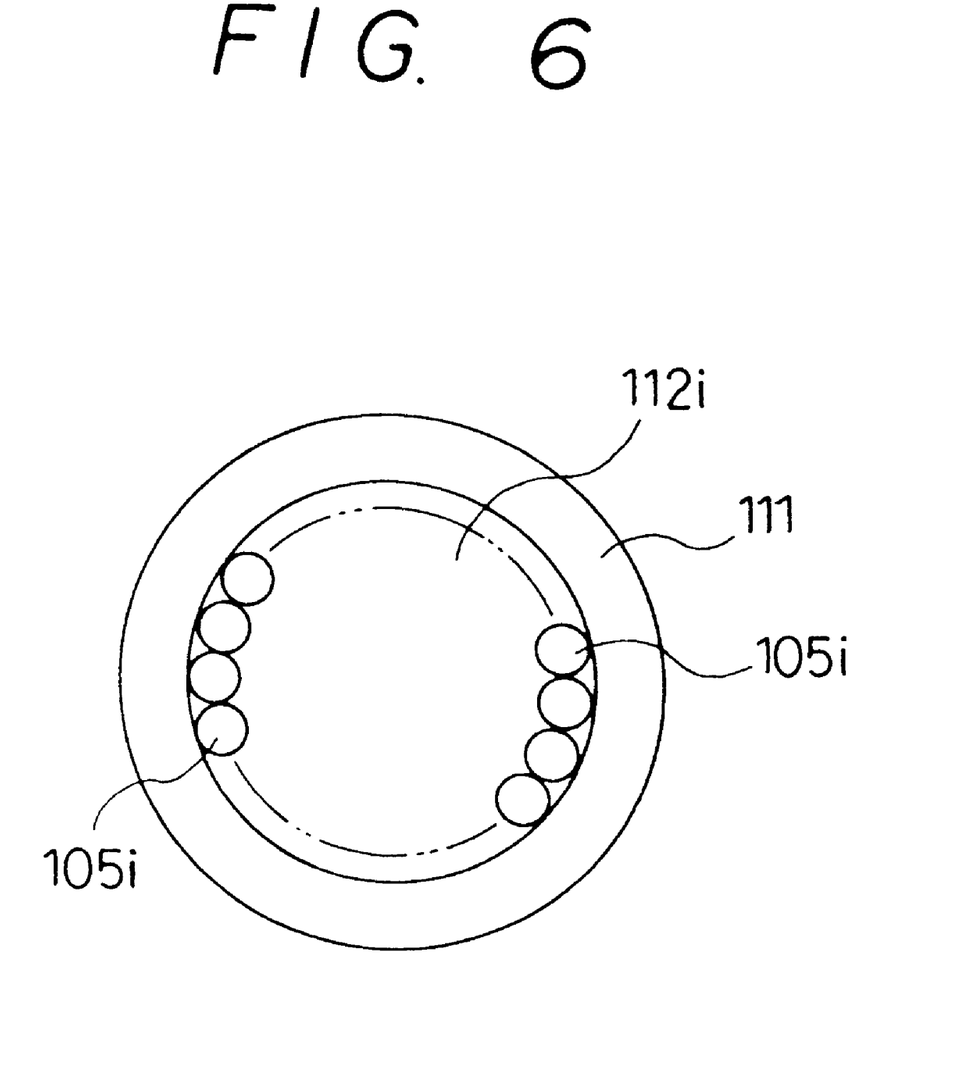
FIG. 6 is an explanatory view showing the relationship between output end faces of optical fibers and an output end face of an image transmitting member.

Leading ends of the optical fibers 105, 105, . . . constituting the light source system are embedded in a fixing ring 111 and located such that their illuminating end faces 105i, 105i, . . . may be located annularly as shown in FIG. 6. The illuminating end faces 105i, 105i, . . . , which are located annularly, face the peripheral edge region of an output end face 112i of an image transmitting member 112, which will be described later.

Specifically, illumination light having been radiated out of the illuminating end faces 105i, 105i, . . . of the respective optical fibers 105, 105, . . . enters from the peripheral edge region of the output end face 112i into the image transmitting member 112, is propagated inside of the image transmitting number 112, and is thus irradiated to the material-to-be-observed M.

As illustrated in FIG. 4, the image transmitting member unit 103 is provided with an elongated protective cylinder 113. A cover glass plate 114, an objective lens 115, and the image transmitting member 112 are located within the protective cylinder 113 in this order from the leading end side. Also, a thread engagement member 116 is secured to the base end portion of the protective cylinder 113 such that the protective cylinder 113 can be releasably mounted on the main body 102.

Figure 7:
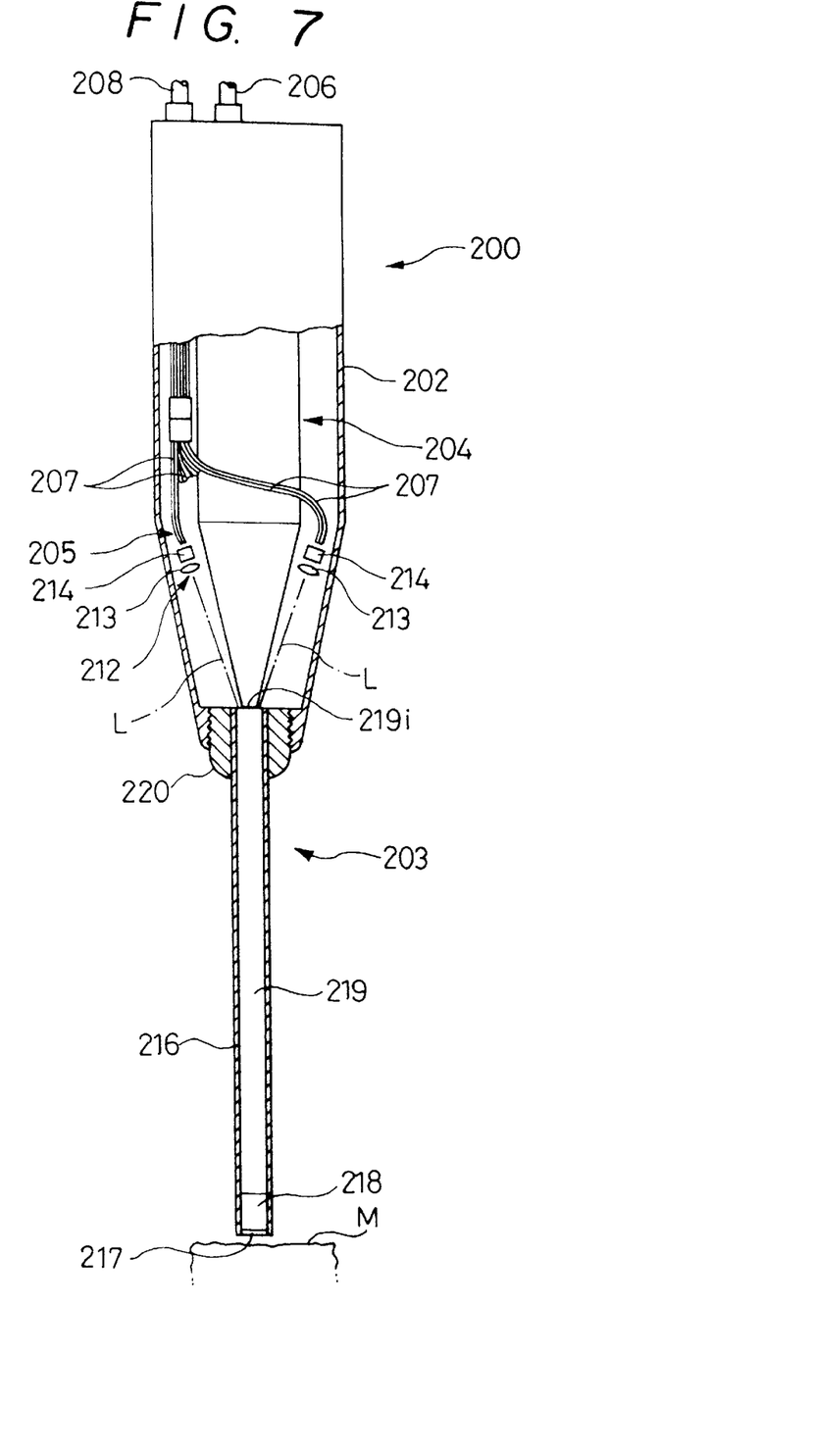
FIG. 7 is a partially sectional side view showing an image pickup section in a third embodiment of the observation apparatus in accordance with the present invention.

Third Embodiment:

In the third embodiment of the observation apparatus in accordance with the present invention, as illustrated in FIG. 7, an image pickup sect ion 200 comprises a main body 202 and an image transmitting member unit 203 in the same manner as that in the second embodiment. The image of the material-to-be-observed M, which has been picked up by the image pickup section 200, is reproduced into a visible image by a observation apparatus body (not shown).

The main body 202 has a cylindrical shape and incorporates therein a camera unit (an image pickup unit) 204 and a light source system unit 205, which constitutes a light source system serving as part of an illuminating system. A signal cable 206, which is connected to the image pickup unit 204, and a light source cable 208, which is composed of a bundle of a plurality of optical fibers 207, 207, . . . included in the light source system unit 205, extend from the main body 202 to the exterior.

Figure 8:
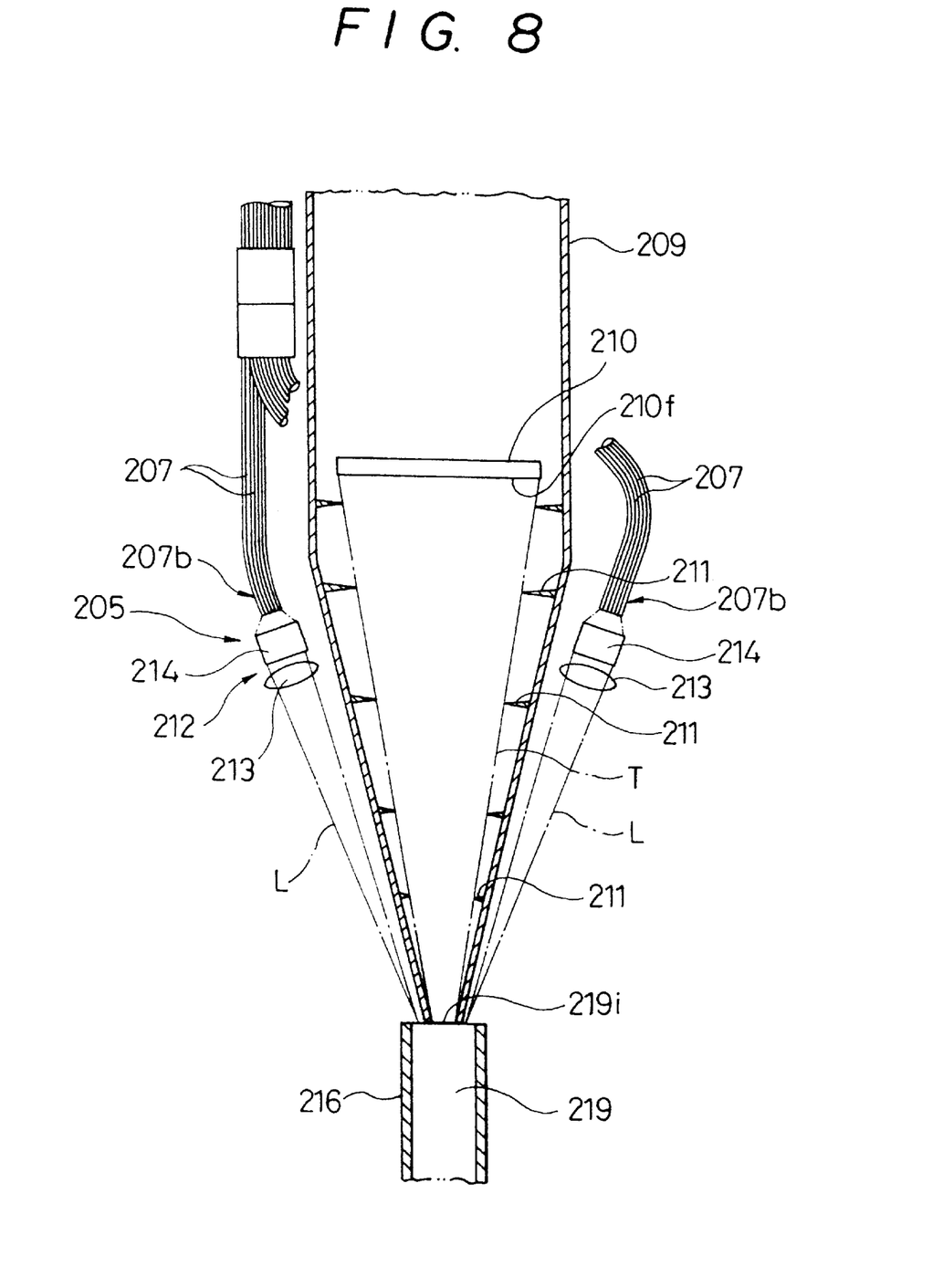
FIG. 8 is an enlarged sectional view showing part of the image pickup section shown in FIG. 7.

As illustrated in FIG. 8, the image pickup unit 204 comprises a light shielding cylinder 209 having a conically narrowed leading end portion. A solid-state image pickup device 210 of the camera unit, stops 211, 211, . . . for preventing flare, and the like, are located within the light shielding cylinder 209.

The light source system unit 205 comprises the plurality of the optical fibers 207, 207, . . . , which guide the illumination light from an exterior light source, and a condensing system unit 212. The condensing system unit 212 condenses the illumination light, which is radiated out of the leading end faces i.e. the illuminating end faces, of the optical fibers 207, 207, . . . , into spots such that the spots may be located annularly at the peripheral edge region of an output end face 219i of an image transmitting member 219, which will be described later.

The condensing system unit 212 comprises an appropriate number of image forming lenses 213, 213, . . . and collinator lenses 214, 214, . . . , which are located so as to correspond respectively to the image forming lenses 213, 213, . . . The image forming lenses 213, 213, . . . and the collimator lenses 214, 214, . . . are mounted on a frame body (not shown). Each of the collimator lenses 214, 214, . . . corresponds to one of optical fiber bundles 207b, 207b, . . . , into which the optical fibers 207, 207, . . . are grouped in units of an appropriate number of fibers. The illumination light L having been condensed by the condensing system unit 212 enters from the peripheral edge region of the output end face 219i into the image transmitting member 219, is propagated inside of the image transmitting member 219, and is thus irradiated to the material-to-be-observed M.

As illustrated in FIG. 7, the image transmitting member unit 203 is provided with an elongated protective cylinder 216. A cover glass plate 217, an objective lens 218, and the distributed index type of the image transmitting member 219 are located within the protective cylinder 216 in this order from the leading end side. Also, a thread engagement member 220 is secured to the base end portion of the protective cylinder 216 such that the protective cylinder 216 can be releasably mounted on the main body 202.

Figure 9:
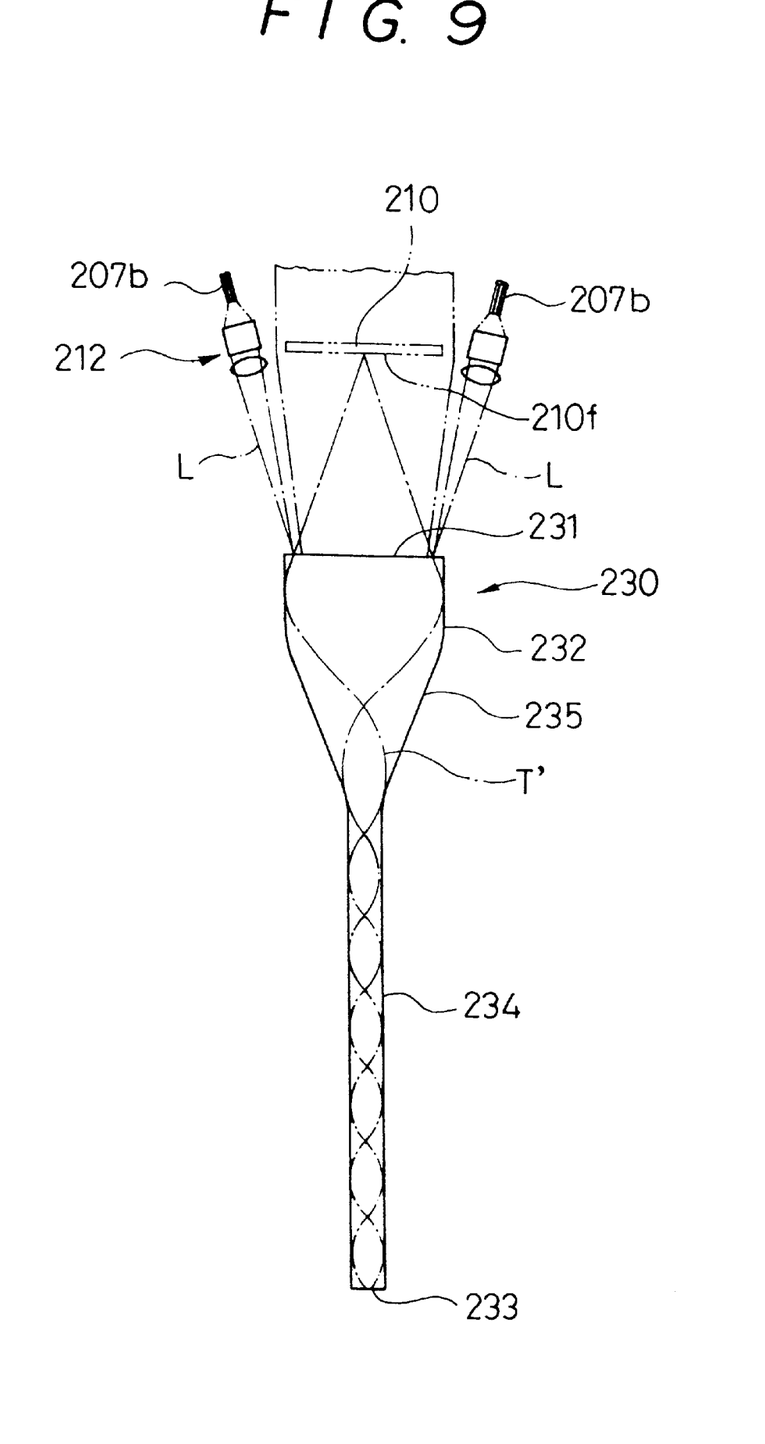
FIG. 9 is a sectional view showing part of an image pickup section in a fourth embodiment of the observation apparatus in accordance with the present invention.

Fourth Embodiment:

In a fourth embodiment shown in FIG. 9, which is a modification of the third embodiment described above, a distributed index type of image transmitting member 230 having a special structure is employed. Specifically, the image transmitting member 230 comprises a short, large-diameter portion 232, the end face of which serves as an output end face 231, and an elongated, small-diameter portion 234, the end face of which serves as an input end face 233. The image transmitting member 230 also includes a continuous diameter change portion 285, in which the diameter decreases continuously from the side of the large-diameter portion 232 towards the side of the small-diameter portion 234.

In the image transmitting member 230, the image is transmitted along an optical path T' indicated by the chained line in FIG. 9. In the small-diameter portion 234, the image having entered from the input end face 233 is transmitted with equal magnification in the same manner as that in an ordinary distributed index type of image transmitting member. The image is gradually enlarged from the continuous diameter change portion 235 to the large-diameter portion 232, and is ultimately formed on a light receiving face 210f of the solid-state image pickup device 210 as an image enlarged with a magnification corresponding to the ratio between the diameters of the output end face 231 and the input end face 233.

The illumination light L coming from the condensing system unit 212 enters from the output end face 231 into the image transmitting member 230. The illumination light L is then propagated inside of the image transmitting member 230 in the direction reverse to the direction of image transmission and is thus irradiated from the input end face 233 to the material-to-be-observed. Specifically, the illumination light having entered from the large-diameter output end face 231 is condensed in the continuous diameter change portion 235 and is then irradiated from the small-diameter input end face 233 to the material-to-be-observed. With the image transmitting member 230 constituted in this manner, the illumination light coming from the condensing system unit 212 can be efficiently entered from the output end face 231. Also, because the image transmitting member itself has the condensing properties, illumination light having a very high intensity can be obtained.

The image transmitting member 230 can be obtained with a stretching process or a dropping process. In the stretching process, a cylindrical intermediate material having a thickness corresponding to the thickness of the large-diameter portion is first formed, softened with heat, and then stretched with predetermined tensile force and speed. In this manner, the image transmitting member having the desired continuous diameter change portion is obtained. In the dropping process, a cladding tube having a shape provided with the desired continuous diameter change portion is formed. A resin for the formation of refractive index distribution is then dropped and loaded into the cladding tube, and the image transmitting member is thereby obtained. As for the resin material to be used in these processes, the techniques disclosed in, for example, Japanese Unexamined Patent Publication Nos. 97302/1992 and 97303/1992 can be utilized.

Figure 10:
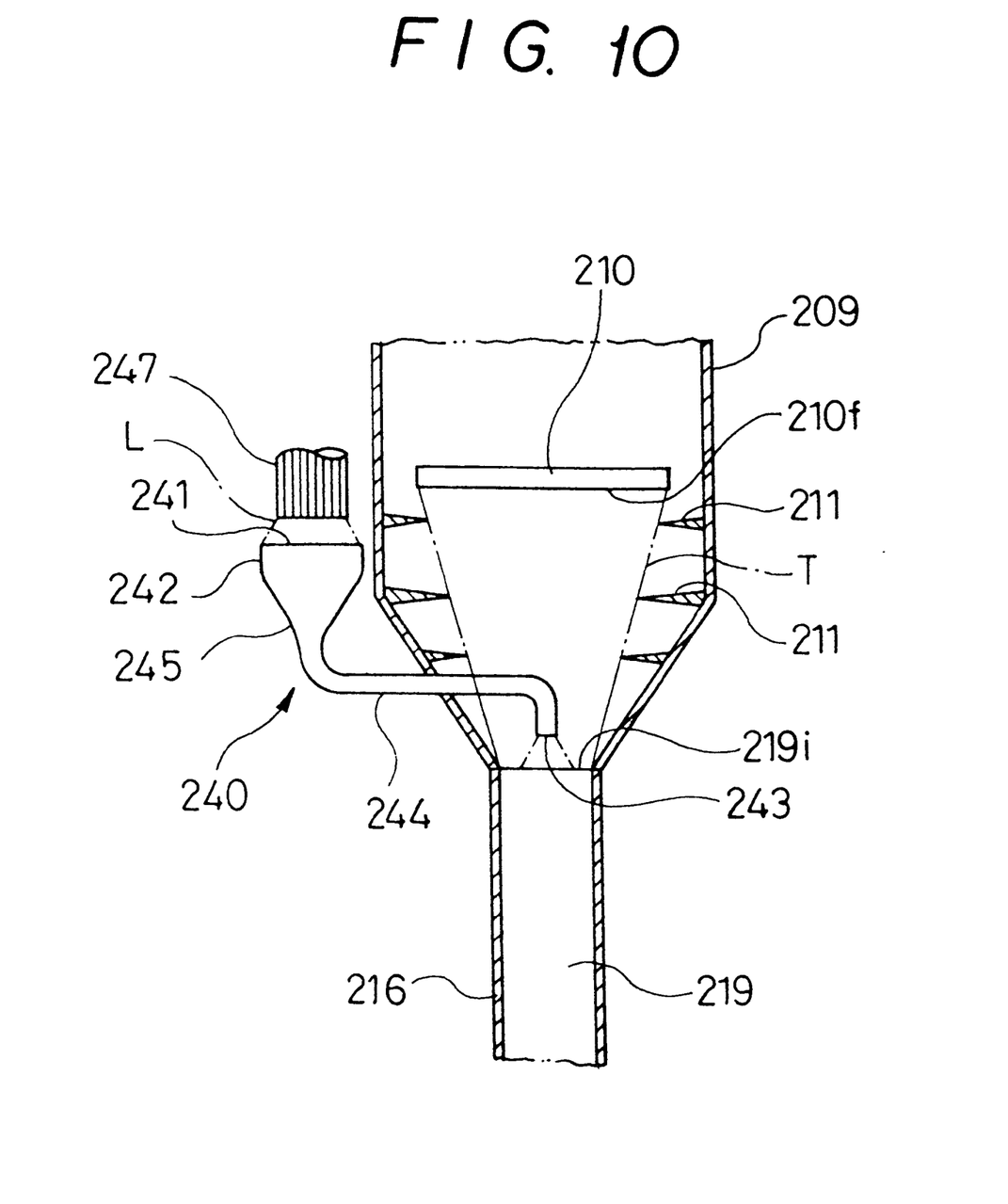
FIG. 10 is a sectional view showing part of an image pickup section in a fifth embodiment of the observation apparatus in accordance with the present invention.

Fifth Embodiment:

In a fifth embodiment shown in FIG. 10, a light transmitting member 240 having the same structure as that of the image transmitting member 230 in the fourth embodiment described above is employed in a condensing system of a light source system.

Specifically, the light transmitting member 240 employed in the condensing system comprises a short, large-diameter portion 242, which has a first end face 241 having a diameter of approximately 1 cm (corresponding to the output end face 231 of the image transmitting member 230), and an elongated, small-diameter portion 244, which has a second end face 243 having a diameter of approximately 0.5 mm (corresponding to the input end face 233 of the image transmitting member 230). Also, a continuous diameter change portion 245 is formed between the large-diameter portion 242 and the small-diameter portion 244. The light transmitting member 240 condenses and transmits the illumination light in the same manner as that of the image transmitting member 230.

The light transmitting member 240 has softness, and its small-diameter portion 244 is bent. The light transmitting member 240 is located between the output end face of an optical fiber bundle 247 and the output end face 219i of the image transmitting member 219 such that the first end face 241 may stand facing the output end face of the optical fiber bundle 247, and such that the second end face 243 may stand facing an approximately center region of the output end face 219i of the image transmitting member 219.

Specifically, the illumination light L coming from the optical fiber bundle 247 enters from the first end face 241 into the light transmitting member 240 and is efficiently condensed by the continuous diameter change portion 245. The illumination light L is then radiated as strong illumination light out of the second end face 243 to the output end face 219i of the image transmitting member 219, propagated inside of the image transmitting member 219, and irradiated to the material-to-be-observed.

Figure 11:
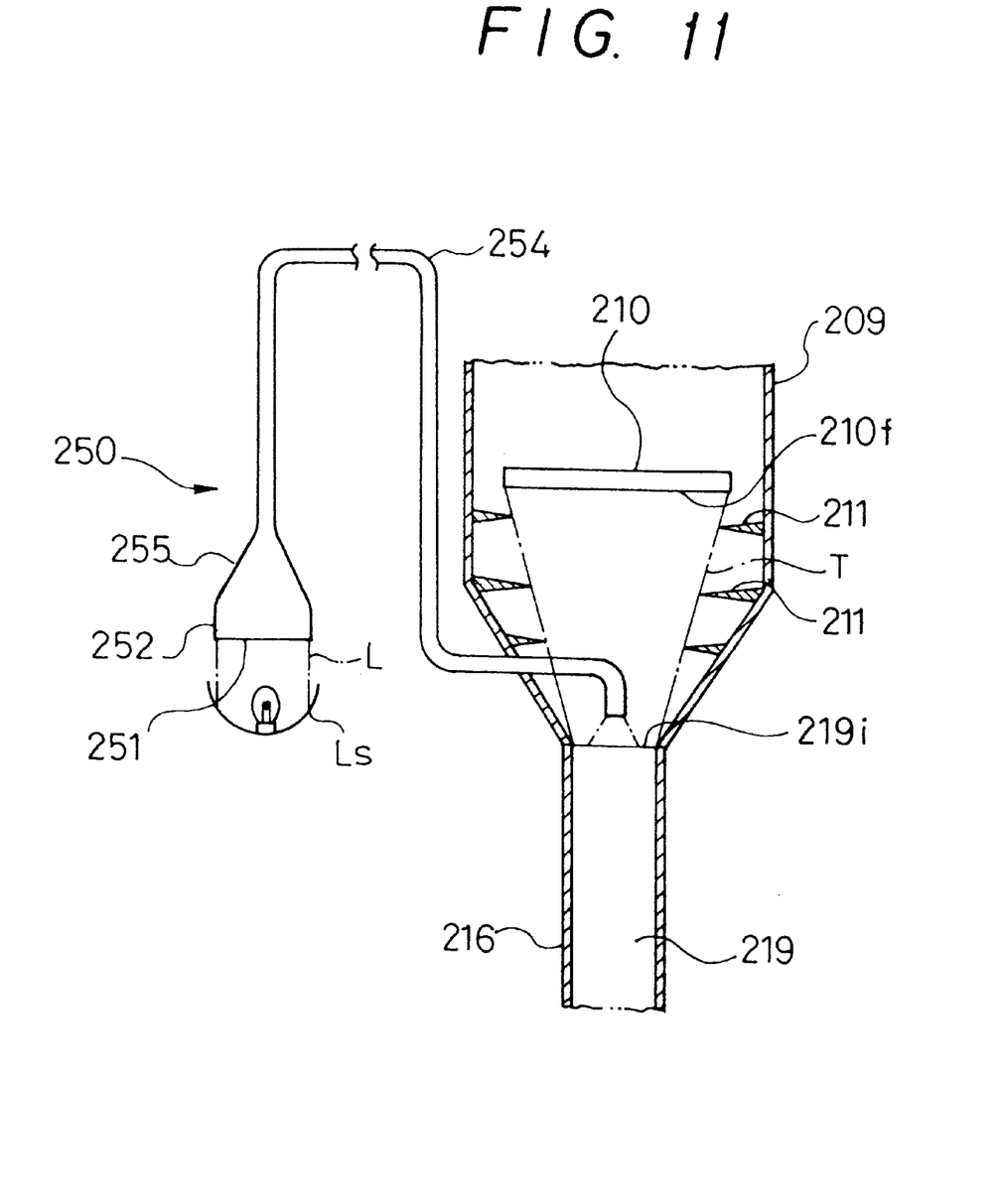
FIG. 11 is a sectional view showing part of an image pickup section in a sixth embodiment of the observation apparatus in accordance with the present invention.

Sixth Embodiment:

In a sixth embodiment shown in FIG. 11, which is a modification of the fifth embodiment described above, a light transmitting member 250 having a sufficiently long small-diameter portion 254 is employed in the light source system. Specifically, in the sixth embodiment, unlike the embodiment shown in FIG. 10 wherein the light transmitting member 240 is employed as the condensing system of the light source system, a large-diameter portion 252 of the light transmitting member 250 falls directly facing an external light source Ls. The illumination light L, which has been produced by the light source Ls and has entered from a first end face 251 of a large-diameter portion 252, is condensed by a continuous diameter change portion 255 and is then guided through the sufficiently long small-diameter portion 254 to the output end face 219i of the image transmitting member 219.

Figure 12:
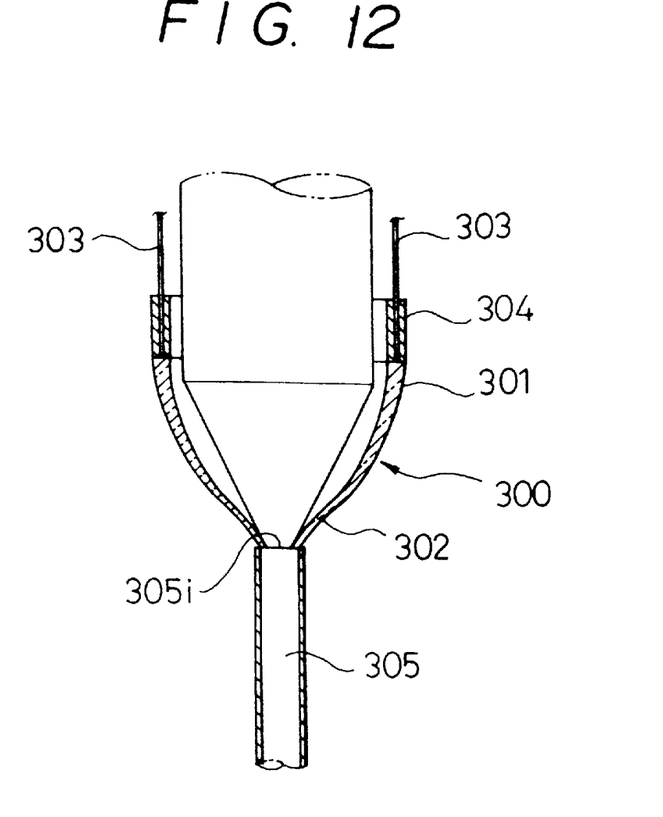
FIG. 12 is a sectional view showing part of an image pickup section in a seventh embodiment of the observation apparatus in accordance with the present invention.

Seventh Embodiment:

In a seventh embodiment, a cylindrical transparent member 300 as shown in FIG. 12 is inserted into the structure of the second embodiment.

Figure 13:
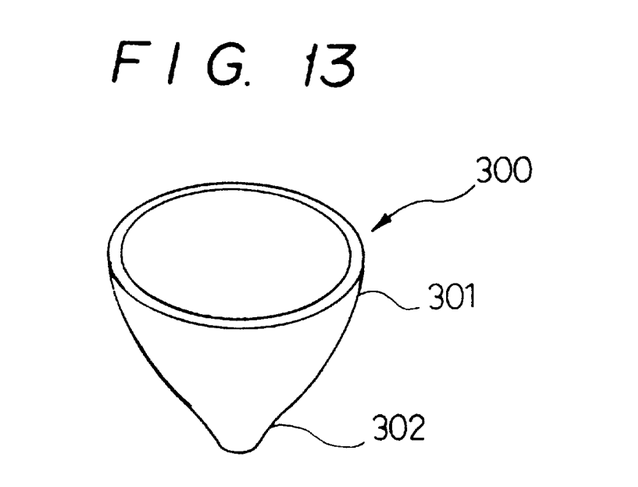
FIG. 13 is a perspective view showing a cylindrical transparent member in a seventh embodiment.

Specifically, the cylindrical transparent member 300 is constituted of a hollow body having a wall thickness of approximately 1 to 2 mm as shown also in FIG. 13 and has a shape such that the diameter may change continuously from a large-diameter portion 301, which is formed on one end side, to a small-diameter portion 302, which is formed on the other end side. The illumination light having entered from an end face of the large-diameter portion 301 is propagated inside of the cylindrical transparent member 300 through repeated reflection according to the continuous change in the diameter and is then radiated out of the small-diameter portion 302.

Leading ends of optical fibers 303, 303, . . . constituting the light source system are embedded in a fixing ring 304 and located such that their illuminating end faces may be located annularly as shown in FIG. 6. The illumination light radiated out of the illuminating end faces passes through the cylindrical transparent member 300 and then enters from the peripheral edge region of an output end face 305i into an image transmitting member 305.

As described above, in the observation apparatus of the present invention, the elongated image transmitting member, which acts as an image transmitting path, also serves as the propagation path for the illumination light. As a result, the site from which an image is to be obtained can be illuminated accurately and efficiently. Further, the slender portion can be made thinner, as well as constituted as a releasable and disposable unit. Therefore, the present invention can greatly contribute to improvement in performance and function of a observation apparatus, such as an endoscope for medical purposes or an apparatus used to observe internal configurations of various structures and equipment.

What is claimed is:

1. An observation apparatus comprising:

a main body;

an illuminating system having a light source for generating illumination light for illuminating a material-to-be-observed;

an elongated image transmitting member having an incident end face for receiving reflected illumination light for forming an image of an imaging range of said material-to-be-observed, said reflected illumination light being said illumination light reflected from said material-to-be-observed, and an output end with an output end face for outputting said reflected illumination light to form said image of said imaging range of said material-to-be-observed, said image transmitting member receiving said illumination light at an area limited to a peripheral edge region of said output end face and transmitting said illumination light out said incident end face to illuminate an illumination range of said material-to-be-observed coinciding with said imaging range, said image transmitting member having a common transmission media for simultaneously transmitting both said illumination light and said reflected illumination light therethrough;

said output end being removably mounted to said main body;

an image pickup device for receiving said reflected illumination light and said image of said material-to-be-observed formed thereby; and said illuminating system including a means for directing said light from said light source in said illuminating system into said area limited to said peripheral edge region of said output end face of said image transmitting member for transmission through said common transmission media and out of said incident end face while said reflected illumination light is simultaneously transmitted through said common transmission media in an opposite direction, thereby illuminating said illumination range coinciding with said imaging range of said material-to-be-observed to fully illuminate said imaging range of said material-to-be-observed.

2. An observation apparatus comprising:

a main body;

an illuminating system having a light source for generating illumination light for illuminating a material-to-be-observed;

an elongated image transmitting member having an incident end face for receiving reflected illumination light for forming an image of an imaging range of said material-to-be-observed, said reflected illumination light being said illumination light reflected from said material-to-be-observed, and an output end with an output end face for outputting said reflected illumination light to form said image of said imaging range of said material-to-be-observed, said image transmitting member receiving said illumination light at an area limited to a peripheral edge region of said output end face and transmitting said illumination light out said incident end face to illuminate an illumination range of said material-to-be-observed coinciding with said imaging range, said image transmitting member having a common transmission media for simultaneously transmitting both said illumination light and said reflected illumination light therethrough;

said output end being removably mounted to said main body;

an image pickup device for receiving said reflected illumination light and said image of said material-to-be-observed formed thereby;

said illuminating system including a means for directing said illumination light into said output end face of said image transmitting member for said transmission through said common transmission media while said reflected illumination light is simultaneously transmitted through said common transmission media in an opposite direction, thereby illuminating said illumination range coinciding with said imaging range of said material-to-be-observed to fully illuminate said imaging range of said material-to-be-observed; and said means for directing said illumination light into said output end face of said image transmitting member directing said illumination light from said light source in said illuminating system and including a plurality of optical fibers arranged for directing said illumination light to said area limited to said peripheral edge region of said output end face of said image transmitting member for reception into said image transmitting member.

3. An observation apparatus comprising:

a main body;

an illuminating system having a light source for generating illumination light for illuminating a material-to-be-observed;

an elongated image transmitting member having an incident end face for receiving reflected illumination light for forming an image of an imaging range of said material-to-be-observed, said reflected illumination light being said illumination light reflected from said material-to-be-observed, and an output end with an output end face for outputting said reflected illumination light to form said image of said imaging range of said material-to-be-observed, said image transmitting member receiving said illumination light at an area limited to a peripheral edge region of said output end face and transmitting said illumination light out said incident end face to illuminate an illumination range of said material-to-be-observed coinciding with said imaging range, said image transmitting member having a common transmission media for simultaneously transmitting both said illumination light and said reflected illumination light therethrough;

said output end being removably mounted to said main body;

an image pickup device for receiving said reflected illumination light and said image of said material-to-be-observed formed thereby;

said illuminating system including a means for directing said illumination light from said illuminating system into said output end face of said image transmitting member for transmission through said common transmission media and out of said incident end face, thereby illuminating said illumination range coinciding with said imaging range of said material-to-be-observed to fully illuminate said imaging range of said material-to-be-observed, while said reflected illumination light is simultaneously transmitted through said common transmission media in an opposite direction; and said means for directing said illumination light into said output end face of said image transmitting member including a plurality of optical fibers directing said illumination light from said light source in said illuminating system to condenser lenses for annularly condensing said illumination light on said area limited to said peripheral edge region of said output end face of said image transmitting member to input said illumination light into said output end face.

4. An observation apparatus comprising:

a main body;

an illuminating system having a light source for generating illumination light for illuminating a material-to-be-observed;

an elongated image transmitting member having an incident end face for receiving reflected illumination light for forming an image of an imaging range of said material-to-be-observed, said reflected illumination light being said illumination light reflected from said material-to-be-observed, and an output end with an output end face for outputting said reflected illumination light to form said image of said imaging range of said material-to-be-observed, said image transmitting member receiving said illumination light at an area limited to a peripheral edge region of said output end face and transmitting said illumination light out said incident end face to illuminate an illumination range of said material-to-be-served coinciding with said imaging range, said image transmitting member having a common transmission media for simultaneously transmitting both said illumination light and said reflected illumination light therethrough;

said output end being removably mounted to said main body;

an image pickup device for receiving said reflected illumination light and said image of said material-to-be-observed formed thereby;

said illuminating system including a means for directing said illumination light from said illuminating system into said output end face of said image transmitting member for transmission through said common transmission media and out of said incident end face while said reflected illumination light is simultaneously transmitted through said common transmission media in an opposite direction, thereby illuminating said illumination range coinciding with said imaging range of said material-to-be-observed to fully illuminate said imaging range of said material-to-be-observed; and said means for directing said illumination light into said output end face of said image transmitting member including a cylindrical condenser lens having a large diameter end and a small diameter end, a diameter of said transparent member changing continuously from said large diameter end to said small diameter end, and said small diameter end being aligned with said output end face so as to direct said illumination light into said area of said output end face limited to said peripheral edge region of said output end face of said image transmitting member.

* * * * *